United States Patent
Stoner et al.

(10) Patent No.: US 6,403,640 B1
(45) Date of Patent: Jun. 11, 2002

(54) METHOD FOR TREATING CHRONIC PROSTATITIS OR CHRONIC PELVIC PAIN SYNDROME

(75) Inventors: Elizabeth Stoner, Westfield; Joanne Waldstreicher, Scotch Plains, both of NJ (US); Curtis J. Nickel, Elginburg (CA); Michel A. Pontari, Lafayette Hill, PA (US)

(73) Assignees: Merck & Co., Inc., Rahway, NJ (US); Temple University of the Commonwealth of Higher Ed., Philadelphia, PA (US)

( * ) Notice: Subject to any disclaimer, the term of this patent is extended or adjusted under 35 U.S.C. 154(b) by 0 days.

(21) Appl. No.: 09/644,998

(22) Filed: Aug. 24, 2000

Related U.S. Application Data
(60) Provisional application No. 60/151,126, filed on Aug. 27, 1999.

(51) Int. Cl.$^7$ ................................................ A61K 31/34
(52) U.S. Cl. .................. 514/473; 514/152; 514/252.16; 514/284; 514/315; 514/323
(58) Field of Search ................................. 514/406, 378, 514/335, 226.5, 473, 252.16, 323, 284, 315, 152

(56) References Cited

U.S. PATENT DOCUMENTS

| | | | |
|---|---|---|---|
| 6,054,455 A | 4/2000 | Guess et al. | |
| 6,136,831 A | 10/2000 | Aotsuka et al. | |

FOREIGN PATENT DOCUMENTS

| | | | |
|---|---|---|---|
| WO | WO-98/06708 | * 2/1998 | |
| WO | WO98/46594 | 10/1998 | |

OTHER PUBLICATIONS

Sorbera et al. Rofecoxib: anti iinflammatory cox–2 inhibitor, AN 1999:150175, (1998).*
Lane, Pain management in osteoarthritis: the role of cox–2 inhibitors, Pub Med (1997).*
Carmichael, E–Drug: Last Posting about Nimesulide, 1999.*
Warner et al., Proc. Natl. Acad. Sci. USA, vol. 96, pp 7563–7568, Jun. 1999.
Nickel et al., J. Urology, vol. 165, No. 5, Program Abstracts Suppl., p. 27, Item #114 (May 2001).
International Chronic Prostatitis Collaborative Research Network, Bethesda (Oct. 24, 2000).
Canale et al. Drugs 46 (Suppl. 1): 147–150, 1993.
Aornink et al. Textbook of Prostatitis, JC Nickel, ed. pp 213–217 (1999).
Canale, et al.–Database Medline, Drugs, Suppl. 1, pp. 147–150, 1993 Abstract only.
Canale, et al.–Database Medline No. 93297754, Andrologia, vol. 25 (3), pp. 163–166, 1993 abstract.
Venturini, et al.–Database Embase, No. 1998077308, Cephalalgia 17/20 (29–30), 1997 abstract.
Melis, et al.–Database Medline–No. 98024769, Minerva Ginecologica, vol. 49 (9), pp. 409–415, 1997 abstract.

* cited by examiner

*Primary Examiner*—Minna Moezie
*Assistant Examiner*—Mojdeh Bahar
(74) *Attorney, Agent, or Firm*—Raynard Yuro; Richard C. Billups; David L. Rose

(57) ABSTRACT

The use of a COX-2 selective inhibitor for the treatment of chronic prostatitis or chronic pelvic pain syndrome is disclosed.

4 Claims, No Drawings

METHOD FOR TREATING CHRONIC PROSTATITIS OR CHRONIC PELVIC PAIN SYNDROME

CROSS-REFERENCE TO RELATED APPLICATIONS

This application is a non-provisional application related to U.S. Application Ser. No.: 60/151,126 filed on Aug. 27, 1999 priority of which is claimed hereunder.

BACKGROUND OF THE INVENTION

Chronic prostatitis or chronic pelvic pain syndrome is an extremely prevalent disease in men (Collins M M, et al., "How common is prostatitis? A national survey of physician visits," *Journal of Urology,* 159:1224–1228 (1998)). Although the epidemiologic evidence is limited, it appears that the prevalence of prostatitis is approximately 2–9% in adult men. It has been suggested that 35–50% of men are affected by prostatitis at some time in life. Approximately 2 million ambulatory patient visits are made annually for prostatitis, accounting for 8% of all visits to urologists and 1% of all visits to primary care physicians. Many men remain symptomatic for much of their lives.

Chronic prostatitis is characterized by evidence of prostatic inflammation and by the presence or absence of white blood cells in prostatic fluid and/or pain associated with the prostate. This syndrome does not exist prior to puberty but has a peak incidence between the ages of 18 and 50. Suggestions as to the origins of these conditions have included a chemical imbalance in the prostate, infection undetected by current microbiological methods and autoimmunity to the prostate gland itself.

Chronic non-bacterial prostatitis and prostatodynia (Chronic Pelvic Pain Syndrome) is characterized by pain and/or discomfort in the genitourinary, pelvic or perineal area and is associated with variable voiding and sexual dysfunction. Chronic nonbacterial prostatitis [Chronic Pelvic Pain Syndrome NIH Category IIIA] is an inflammatory and painful condition of unknown etiology characterized by excessive inflammatory cells in prostatic secretions despite a lack of documented urinary tract infections, and negative bacterial cultures of urine and prostatic secretions. Prostatodynia [Chronic Pelvic Pain Syndrome NIH Category IIIB] is a painful condition of unknown etiology characterized by a decided lack of inflammatory cells in prostatic secretions, no documented urinary tract infections and negative bacterial cultures in urine and prostatic secretions. Chronic non-bacterial prostatitis is more common than bacterial prostatitis. Symptoms mimic those of chronic bacterial prostatitis. Patients usually show an increase in the number of white blood cells and oval fat bodies in their expressed prostatic secretions. However, they rarely have a history of urinary tract infection, and lower-tract localization cultures fail to reveal a pathogenic organism.

Currently, there are no established treatments for chronic prostatitis. Antibiotics are often prescribed empirically, but with little evidence of efficacy. Alpha blockers are sometimes prescribed, but their efficacy has not been established. Hot sitz baths and anticholinergic drugs can generally be employed to provide some symptomatic relief.

Although the present invention is not limited to a specific mechanism of action, it is noted that COX-2 expression is increased in prostatic tissue involved in chronic prostatitis.

COX-2 selective inhibitors can be administered alone as well as in combination with other active agents. In accordance with the present invention, administration of a COX-2 selective inhibitor reduces both the inflammation and pain that are associated with chronic prostatitis.

SUMMARY OF THE INVENTION

The present invention relates to the use of a COX-2 selective inhibitor for the treatment or prevention of chronic prostatitis or chronic pelvic pain syndrome comprising the administration of a COX-2 selective inhibitor in an amount effective to treat or prevent chronic prostatitis.

DESCRIPTION OF THE INVENTION

The present invention relates to a method of treating or preventing chronic prostatitis or chronic pelvic pain syndrome in a mammalian patient in need of such treatment or prevention, comprising administering to said patient, and effective amount of a COX-2 selective inhibitor.

As used herein, COX-2 selective inhibitors refers to non-steroidal antiinflammatory drugs that selectively inhibit the enzyme COX-2 in preference to COX-1. Examples include celecoxib, parecoxib, rofecoxib, valdecoxib, meloxicam, flosulide, nimesulide, MK-663, NS 398, DuP 697, SC-58125, SC-58635, and RS 57067. Examples of compounds that are useful in this regard are shown below.

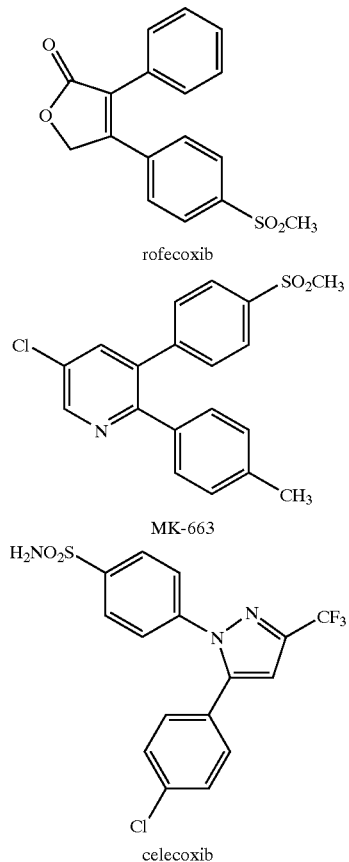

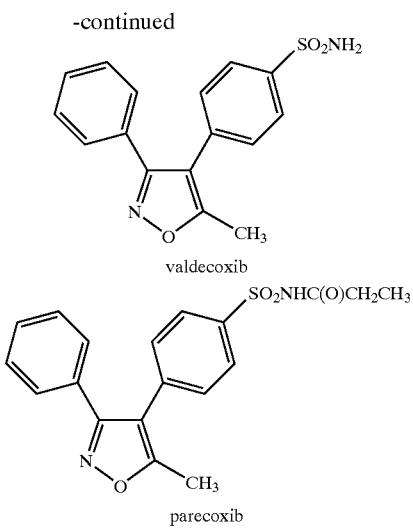

valdecoxib parecoxib

In a particular embodiment, the present invention provides a method for treating or preventing chronic nonbacterial prostatitis in a mammalian patient comprising the administration of a COX-2 selective inhibitor in an amount effect to treat or prevent chronic nonbacterial prostatitis.

It will be recognized by those skilled in the art from the teachings herein that there are numerous compounds which are useful in combination with COX-2 selective inhibitors for treating or preventing chronic prostatitis, which as used herein includes chronic prostatitis, chronic nonbacterial prostatitis, prostatodynia, congestive prostatitis, epididymitis, post-vasectomy pain and inflammation and/or urethritis. In these combinations, the COX-2 selective inhibitor and the other therapeutic agent may be independently present in reduced dosage amounts such as from about one one-hundredth of the usual adult dose, up to as high as a normal adult dose, which is normally effective when these compounds are used singly. In such combination therapy, the COX-2 selective inhibitor may be administered with the other therapeutic agent (e.g., concurrently, concomitantly, sequentially, or in a unitary formulation) such that their therapeutic effects overlap.

The COX-2 selective inhibitor may be administered in combination with an alpha blocker, especially an alpha-1a blocker, a 5-alpha reductase inhibitor, a prostate specific antigen conjugate, an antibiotic, in particular a carbapenem antibiotic, an anticholinergic agent, a second COX-2 selective inhibitor, a topical urinary analgesic and the like.

For treating or preventing chronic pelvic pain syndrome, including e.g., nonbacterial prostatitis, acute or chronic prostatitis, acute bacterial prostatitis, prostatodynia, congestive prostatitis, epididymitis, post-vasectomy pain and inflammation and/or urethritis in a patient, the COX-2 selective inhibitor may be given in combination with additional compounds such as: an alpha blocker, especially an alpha-1a blocker, such as doxazosin, indoramin, prazosin, tamsulosin or terazosin; a 5-alpha reductase inhibitor, such as dutasteride or finasteride, especially a type 2 5-alpha reductase inhibitor, a dual 5-alpha reductase inhibitor, or combinations of type 1 and type 2 5-alpha reductase inhibitors; a prostate specific antigen conjugate; an antibiotic, such as, e.g., amikacin, amoxicillin, ampicillin, carbenicillin, cefaclor, cefadroxil, cefamandole, cefazolin, cefoxitin, cephalexin, Rocefin®, cephalothin, cephapirin, cephradine, ciprofloxacin, cotrimoxazole, demeclocycline, doxycycline, erythromycin, gentamicin, kanamycin, methenamine hippurate, methenamine mandelate, minocycline, nalidixic acid, nitrofurantoin, norfloxacin, ofloxacin, sulfamethoxazole, sulfonamides, tetracycline, ticarcillin, tobramycin, trimethoprim or trimethoprim-sulfamethoxazole, in particular a carbapenem antibiotic such as imipenem, meropenem and the like; anticholinergic agents, such as atropine, hyoscyamine, flavoxate, propantheline or oxybutynin; an analgesic, such as acetaminophen; ketorolac tromethamine; a diuretic such as hydrochlorothiazide, spironolactone or spironolactone with hydrochlorothiazide; trovafloxacin; a corticosteroid;; or a topical urinary analgesic, such as phenazopyridine, and salts thereof, and combinations thereof, and the like and combinations thereof.

Typically, the individual daily dosages for these combinations range from about one-fifth of the minimally recommended clinical dosages to the maximum recommended dosage levels.

Naturally, dosages may be adjusted as necessary to permit divided daily dosages and, as noted above, dosages vary depending on the nature and severity of the disease, weight of patient, special diets and other factors. These combinations may be formulated into pharmaceutical compositions as known in the art and as discussed herein.

The dosage of active ingredient in the compositions of this invention may also be varied as necessary such that a suitable dosage form is obtained. The active ingredient may be administered to patients (animals and human) in need of such treatment in dosages that provide optimal pharmaceutical efficacy.

The appropriate dosage level will generally be from about 0.01 µg to about 50 mg per kg patient body weight per day, which may be administered in single or multiple doses. Preferably, the dosage level will be about 0.1 µg to about 25 mg/kg per day; more preferably about 0.5 µg to about 10 mg/kg per day. For example, for treating or preventing chronic nonbacterial prostatitis or prostatodynia or ameliorating the symptoms attendant to chronic nonbacterial prostatitis or prostatodynia in a patient, a suitable dosage level is about 0.1 µg to 25 mg/kg per day, preferably about 0.5 µg to 10 mg/kg per day, and especially about 1 µg to 5 mg/kg per day. In larger mammals, for example humans, a typical indicated dose is about 300 µg to 400 mg orally. A compound may be administered on a regimen of several times per day, for example 1 to 4 times per day, preferably once or twice per day. When using an injectable formulation, a suitable dosage level is about 0.1 µg to 10 mg/kg per day, preferably about 0.5 µg to 5 mg/kg per day, and especially about 1 µg to 1 mg/kg per day. In larger mammals, for example humans, a typical indicated dose is about 100 µg to 100 mg i.v. A compound may be administered on a regimen of several times per day, for example 1 to 4 times per day, preferably once or twice per day, and more preferably once a day.

A particularly preferred subclass of COX-2 selective inhibitors used in the present invention are those compounds which are orally active and long acting. Such compounds can be administered once daily. The use of this subclass of compounds for treating or preventing acute or chronic prostatitis, chronic nonbacterial prostatitis, acute bacterial prostatitis, prostatodynia, congestive prostatitis, epididymitis, post-vasectomy pain and inflammation and/or urethritis, especially chronic nonbacterial prostatitis or prostatodynia, or ameliorating the symptoms attendant to chronic nonbacterial prostatitis, prostatodynia, congestive prostatitis, epididymitis, post-vasectomy pain and inflammation and/or urethritis, especially chronic nonbacterial prostatitis or prostatodynia, in a patient represents a further aspect of the present invention.

Thus, the present invention provides the use of a COX-2 selective inhibitor in an oral, once-a-day dosage form for treating or preventing acute or chronic prostatitis, chronic nonbacterial prostatitis, acute bacterial prostatitis, prostatodynia, congestive prostatitis, epididymitis, post-vasectomy pain and inflammation and/or urethritis, especially chronic nonbacterial prostatitis or prostatodynia, or ameliorating the symptoms attendant to chronic nonbacterial prostatitis, acute bacterial prostatitis, prostatodynia, congestive prostatitis, epididymitis, post-vasectomy pain and inflammation and/or urethritis, especially chronic nonbacterial prostatitis or prostatodynia, in a patient. The compounds thus exhibit advantageous benefits when compared to conventional methods for treating or preventing chronic nonbacterial prostatitis, prostatodynia, congestive prostatitis, epididymitis, post-vasectomy pain and inflammation and/or urethritis in a patient.

It will be appreciated to those skilled in the art that reference herein to treatment extends to prophylaxis (prevention) as well as the treatment of the noted diseases/disorders and symptoms. Because the specific diagnosis of chronic prostatitis in a particular patient may be difficult, the patient may benefit from the prophylactic administration of the compound in accordance with the present invention.

While the invention has been described herein with reference to certain particular embodiments, those skilled in the art will appreciate that various modifications may be made without departing from the spirit and scope of the present invention. It is intended, therefore, that the invention be defined by the scope of the claims which follow and that such claims be interpreted as broadly as is reasonable.

What is claimed is:

1. A method of treating chronic prostatitis in a mammalian patient suffering from chronic prostatitis, comprising administering to said patient a COX-2 selective inhibitor in an amount that is effective to treat chronic prostatitis, wherein the COX-2 selective inhibitor is:

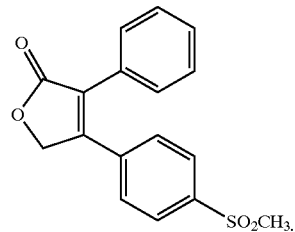

2. A method in accordance with claim 1 wherein the COX-2 selective inhibitor is employed in combination with an agent selected from the group consisting of: alpha-1a blockers, 5-alpha reductase inhibitors, anticholinergic agents, antibiotics and prostate specific antigen conjugates.

3. A method of treating chronic pelvic pain syndrome in a mammalian patient suffering from chronic pelvic pain syndrome, comprising administering to said patient a COX-2 selective inhibitor in an amount that is effective to treat chronic pain syndrome, wherein the COX-2 selective inhibitor is:

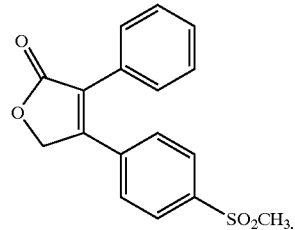

4. A method in accordance with claim wherein the COX-2 selective inhibitor is employed in combination with an agent selected from the group consisting of: alpha-1a blockers, 5-alpha reductase inhibitors, anticholinergic agents, antibiotics and prostate specific antigen conjugates.

* * * * *